(12) United States Patent
Bacher et al.

(10) Patent No.: US 8,906,014 B2
(45) Date of Patent: Dec. 9, 2014

(54) MEDICAL INSTRUMENT WITH ENDOSCOPE

(75) Inventors: Uwe Bacher, Tuttlingen (DE); Gérard Barki, Geneva (CH)

(73) Assignee: Karl Storz GmbH & Co. KG (DE)

(*) Notice: Subject to any disclaimer, the term of this patent is extended or adjusted under 35 U.S.C. 154(b) by 1572 days.

(21) Appl. No.: 11/409,540

(22) Filed: Apr. 21, 2006

(65) Prior Publication Data

US 2006/0247495 A1  Nov. 2, 2006

Related U.S. Application Data

(63) Continuation of application No. PCT/EP2004/012028, filed on Oct. 25, 2004.

(30) Foreign Application Priority Data

Oct. 24, 2003 (DE) .................................. 103 49 825

(51) Int. Cl.
| | |
|---|---|
| A61B 18/14 | (2006.01) |
| A61B 1/00 | (2006.01) |
| A61B 17/22 | (2006.01) |
| A61B 17/00 | (2006.01) |
| A61B 18/00 | (2006.01) |
| A61B 17/29 | (2006.01) |
| A61B 19/00 | (2006.01) |

(52) U.S. Cl.
CPC . *A61B 17/22031* (2013.01); *A61B 2017/00292* (2013.01); *A61B 18/1445* (2013.01); *A61B 2018/00982* (2013.01); *A61B 17/2909* (2013.01); *A61B 2019/5217* (2013.01); *A61B 17/29* (2013.01)
USPC .............................................. 606/46; 600/104

(58) Field of Classification Search
CPC ...................... A61B 18/14; A61B 2018/00166; A61B 18/009582; A61B 2017/00292; A61B 2019/5217; A61B 17/29; A61B 17/2909; A61B 17/22031; A61B 18/1445
USPC .......... 606/50–52, 46–48; 600/102, 104–106, 600/114
See application file for complete search history.

(56) References Cited

U.S. PATENT DOCUMENTS

| 2,004,559 | A | * | 6/1935 | Wappler | ........................... 606/46 |
| 3,299,883 | A | | 1/1967 | Rubens | ......................... 600/102 |

(Continued)

FOREIGN PATENT DOCUMENTS

| DE | 33 37 016 | 12/1984 |
| DE | 40 42 102 | 3/1998 |

(Continued)

OTHER PUBLICATIONS

International Search Report; Feb. 9, 2005; 3 pages.

(Continued)

*Primary Examiner* — Michael Peffley
*Assistant Examiner* — Samantha Good
(74) *Attorney, Agent, or Firm* — St. Onge Steward Johnston & Reens LLC (57) ABSTRACT

A medical instrument comprises a shaft, a work element at the distal end of the shaft, a handle with at least one movable part for actuating the work element and a securing element for securing an endoscope which has an endoscope shaft and an eyepiece. The distal end of the endoscope is able to be arranged in the area of the distal end of the shaft, and the proximal end of the endoscope is able to be arranged in the area of the handle of the instrument, and the endoscope is displaceable in the longitudinal direction of the shaft. The securing element is designed in such a way that the endoscope can be arranged on the outside of the instrument, the eyepiece of the endoscope, in the state when the latter is arranged on the instrument, lying outside the longitudinal axis of the shaft of the instrument.

15 Claims, 4 Drawing Sheets

(56) References Cited

U.S. PATENT DOCUMENTS

| | | | |
|---|---|---|---|
| 4,607,620 A | 8/1986 | Storz | 128/4 |
| 4,759,348 A * | 7/1988 | Cawood | 600/102 |
| 5,226,908 A | 7/1993 | Yoon | 606/141 |
| 5,300,069 A * | 4/1994 | Hunsberger et al. | 606/37 |
| 5,667,472 A | 9/1997 | Finn et al. | 600/104 |
| 5,827,323 A | 10/1998 | Klieman et al. | 606/205 |
| 5,984,939 A * | 11/1999 | Yoon | 606/170 |
| 6,419,626 B1 | 7/2002 | Yoon | 600/109 |
| 2002/0068935 A1* | 6/2002 | Kortenbach et al. | 606/46 |
| 2002/0151890 A1* | 10/2002 | Scholer et al. | 606/48 |
| 2003/0144661 A1* | 7/2003 | Brommersma et al. | 606/46 |
| 2007/0038215 A1* | 2/2007 | Hahn | 606/46 |

FOREIGN PATENT DOCUMENTS

| | | |
|---|---|---|
| DE | 298 23 913 | 2/2000 |
| EP | 0 117 894 | 9/1989 |
| WO | WO 02/094341 | 11/2002 |

OTHER PUBLICATIONS

International Preliminary Report on Patentability, Jul. 15, 2008, 6 Pages.

* cited by examiner

MEDICAL INSTRUMENT WITH ENDOSCOPE

CROSS-REFERENCE TO RELATED APPLICATIONS

The present application is a continuation of pending International Patent Application PCT/EP2004/012028 filed on Oct. 25, 2004 which designates the United States, and which claims priority of German patent application No. 103 49 825.7 filed on Oct. 24, 2003.

BACKGROUND OF THE INVENTION

The present invention generally relates to medical instruments, in particular such medical instruments which may be coupled with an endoscope.

Medical instruments on which an endoscope is mounted in a displaceable manner are known, for example, from documents DE 40 42 102 C2 or EP 0 117 894 A2.

A large number of medical instruments have been developed to keep pace with the increasing application of minimally invasive surgery. In minimally invasive surgery, operations are performed only through a very small incision in the human body.

An operation performed in a minimally invasive manner is monitored using one or more endoscopes which are advanced to the operating site in the body via the same opening or another opening.

However, the use of a medical instrument and of an endoscope independent of the latter has the disadvantage that the relative position of the endoscope with respect to the instrument changes when one of them moves, thus also changing the view afforded to the operating surgeon. This is tiring for the operating surgeon, especially when performing complicated procedures.

Moreover, since an operation is generally not monitored in the form of a stereo image, the relative position of the endoscope with respect to the instrument and of the instrument with respect to the operating site can often be assessed only with difficulty.

Furthermore, the use of a medical instrument and of an endoscope independent of the latter makes it difficult for operations to be performed by just one person, since at least one assistant is normally needed to guide the endoscope.

For this reason, medical systems have been developed which comprise a medical instrument to which an endoscope is coupled.

Such a system is described in document U.S. Pat. No. 4,759,348, for example. In the system described in this document, the distal end of a flexible endoscope is secured at the distal end of a medical instrument. The system is distinguished by great mechanical simplicity. Moreover, the endoscope can be designed such that it can be fitted on any desired medical instrument.

However, the endoscope is secured only at the distal end of the shaft, which results in a significant increase in the instrument diameter. This makes insertion of the medical instrument into the body much more difficult.

Moreover, in the event of a movement of the movable parts of the medical instrument, this known endoscope does not automatically follow the movement. If the medical instrument therefore has a work element which is displaceable along the longitudinal axis relative to the instrument shaft, the endoscope is not displaced too. This means that the view of the work element afforded to the operating surgeon changes as the work element moves. This in turn makes precise use of the work element difficult.

The document U.S. Pat. No. 5,667,472 describes a similar system in which optical fibers are routed along the whole shaft of the medical instrument. In this way, the instrument diameter is increased barely perceptibly, and both the insertion and also the maneuvering of the instrument during the operation are made much easier.

In this medical system too, however, the endoscope does not follow the movement of the work element of the medical instrument, and this leads to the problems described above.

Document DE 40 42 102 C2 describes a medical instrument into which an endoscope is integrated. The endoscope is in this case operatively connected to the work element of the medical instrument and is displaced in synchrony with the displacement of the work element. The shaft of the endoscope in this case lies in the inside of the shaft of the instrument. The eyepiece of the endoscope is arranged at the proximal end of the instrument, such that the longitudinal axis of the eyepiece coincides with the shaft axis of the instrument.

However, this system has the disadvantage that the endoscope is an integral component part of the medical instrument. Therefore, for each new medical instrument, an endoscope also has to be procured.

Integrating the endoscope into the medical instrument also makes it difficult to dismantle for cleaning and sterilizing purposes. Moreover, this construction proves unsuitable for many HF surgical instruments.

Since, in HF instruments, the work element and the associated conductors for the HF voltage regularly have to be removed for replacement or for sterilization, these are generally designed as straight wires with tools at the distal end. The wires can be introduced from the distal end into the shaft and are secured at the proximal end with a clip contact. Also arranged at the proximal end is the connector for the external feed line of the HF voltage. In HF instruments of this kind, therefore, the space for arranging an endoscope optical system is greatly restricted at the proximal end.

Document EP 0 117 894 A2 describes an instrument similar to the one described in DE 40 42 102 C2. The main difference is that the endoscope is guided inside a medical grasping instrument.

SUMMARY OF THE INVENTION

It is an object of the invention to make available a medical instrument which can be coupled in a displaceable manner to any desired endoscope.

According to an aspect of the invention, a medical instrument is provided, comprising a shaft having a distal end and a longitudinal axis, a work element arranged at the distal end and the shaft, and a handle having at least one moveable part for actuating the work element. A securing element is provided for securing an endoscope having an endoscope shaft and an eyepiece such that a distal end of the endoscope shaft being able to be arranged in the area of the distal end of the shaft and a proximal end of the endoscope being able to be arranged in the area of the handle, and that the endoscope is displaceable in direction of the longitudinal axis of the shaft. The securing element is designed in such a way that the endoscope can be arranged on an outside of the instrument, the eyepiece of the endoscope, in the state when the endscope is arranged on the instrument, lying outside the longitudinal axis of the shaft of the instrument.

By means of the securing element on the outside of the instrument, an instrument according to the invention can be connected to any desired endoscope. In this way, for example, a single endoscope can be coupled to a multiplicity of medical instruments, which leads to considerable cost savings. Furthermore, an already existing endoscope can be connected to any desired new instrument according to the invention.

In this case, if the instrument becomes worn, it also suffices to replace only the instrument.

By virtue of the fact that the securing element is designed in such a way that the eyepiece of the endoscope lies outside the longitudinal axis of the shaft of the instrument, the endoscope can be adapted to the shape of the medical instrument. Thus, in particular, an HF instrument, which at its proximal end has a connector for an external HF line, can be equipped with an endoscope.

The displaceability of the endoscope relative to the medical instrument is fully maintained, however.

In a preferred embodiment, the work element comprises at least one electrode that can be acted upon with HF voltage, the work element preferably being designed as a bipolar work element and further preferably as bipolar forceps.

In modern minimally invasive surgery, instruments are often used whose work elements are designed as an electrode or electrodes acted upon with HF voltage. Such instruments are often designed as bipolar instruments, for example as bipolar forceps.

These instruments can be used, for example, to cut tissue and at the same time to arrest bleeding at the operating site.

In a further preferred embodiment, the work element communicates with an electrical contact at the proximal end of the instrument, the electrical contact lying on the longitudinal axis of the shaft.

Since the work elements that can be acted upon by HF voltage, and the HF voltage conductors communicating with them, often have to be removed from the medical instrument because of wear or for sterilization, it has proven expedient to configure the conductors for the HF voltage as straight wires at whose distal end the work elements are located. In this way, the conductors, and the work elements connected to them, can be easily introduced into the shaft at the distal end of the shaft and can then be secured at the proximal end of the instrument.

In this connection, it has proven most expedient if the contacts for supply of the external HF voltage are arranged axially in the longitudinal axis of the shaft. By means of the present invention, the combination of such an HF instrument and an endoscope is now permitted because the eyepiece of the endoscope to be arranged thereon lies outside the longitudinal axis of the instrument shaft, with the result that the HF connector can be arranged on the longitudinal axis of the shaft.

In one embodiment of the aforementioned measure, the work element is connected to the electrical contact via at least one conductor, it being possible for the work element, the at least one conductor and the electrical contact to be removed as one unit from the shaft.

This measure makes dismantling and assembling of the medical instrument much easier, since the often thin conductors no longer have to be inserted in the instrument into the electrical contact.

Furthermore, this measure allows the current-carrying components of the instrument to be assembled and tested separately and then inserted as one unit into the instrument. It is thus easier to ensure the functional reliability of the current-carrying components of the instrument.

In a further preferred embodiment, the electrical contact is designed as a plug connection for attachment of an external cable, the plug connection being arranged in a substantially rectilinear continuation of the shaft.

Arranging the plug connection in a substantially rectilinear continuation of the shaft means that the freedom of movement of an operating surgeon is impeded to a much lesser extent than in the case of supply lines that protrude laterally from the instrument.

In a preferred embodiment of the invention, a guide tube is arranged on the shaft of the instrument and extends parallel to the shaft, and the endoscope shaft can be inserted into it.

The effect of such a guide tube is that displacement of the endoscope does not catch surrounding tissue and damage it.

In a further preferred embodiment, the guide tube for receiving the endoscope is formed by a channel in the shaft.

This measure has the advantage that the instrument diameter is increased only slightly. Moreover, this configuration has only a small number of corners and niches in which bacteria can accumulate and which are difficult to clean.

In a further preferred embodiment, the instrument comprises an irrigation attachment piece, so that an inside of the shaft and of the guide tube can be simultaneously irrigated.

This measure has the advantage that, in a structurally simple manner, the work elements, and the optical system of an endoscope to be fitted, and the area surrounding the operating site, can all be irrigated.

In a preferred embodiment, the securing element is in operative connection with the movable part of the handle.

This measure has the advantage that the endoscope and the work element can be displaced with one hand and in a single movement. In this way, it is also possible to avoid unwanted displacement of the endoscope relative to the shaft of the instrument. As a result, the fatigue experienced when using the medical instrument with the endoscope in the course of operations is greatly reduced.

In a further preferred embodiment, the securing element is designed in such a way that, upon actuation of the handle, the distal end of the endoscope remains at a constant distance from the distal end of the work element.

This measure is especially advantageous because the endoscope automatically tracks the work element and, in this way, the operating surgeon always has the same view of the work element. This greatly enhances the precision of operations performed with a medical system according to the invention. In addition, no further measures are needed for positioning and tracking of the endoscope.

In a further preferred embodiment, the handle of a medical instrument according to the invention comprises at least one grip protruding laterally from the instrument.

A laterally protruding grip facilitates precise turning of the medical instrument about its longitudinal axis during an operation.

Moreover, by means of a laterally protruding grip, the angle between said grip and the eyepiece of the endoscope can be significantly increased, which greatly simplifies the use of the grip and also of the eyepiece of the endoscope during an operation.

In a further preferred embodiment of the abovementioned measure, the grip of the handle is designed in the manner of scissor grip parts.

Scissor grip parts have proven especially advantageous, from the ergonomic point of view, for one-handed use of a medical instrument according to the invention.

In a further preferred embodiment, the securing element is designed in such a way that a shaft of the endoscope has a curvature in a proximal portion and is flexible or bendable at least in the curved area.

Further advantages and features will become clear from the following description and from the attached drawing.

It will be appreciated that the features mentioned above, and the features still to be explained below, can be used not just in the respectively cited combination, but also in other combinations or singly, without departing from the scope of the present invention.

BRIEF DESCRIPTION OF THE DRAWINGS

Illustrative embodiments of the invention are depicted in the drawings and are described below with reference to this drawings, in which.

DETAILED DESCRIPTION OF THE INVENTION

Figure 1:
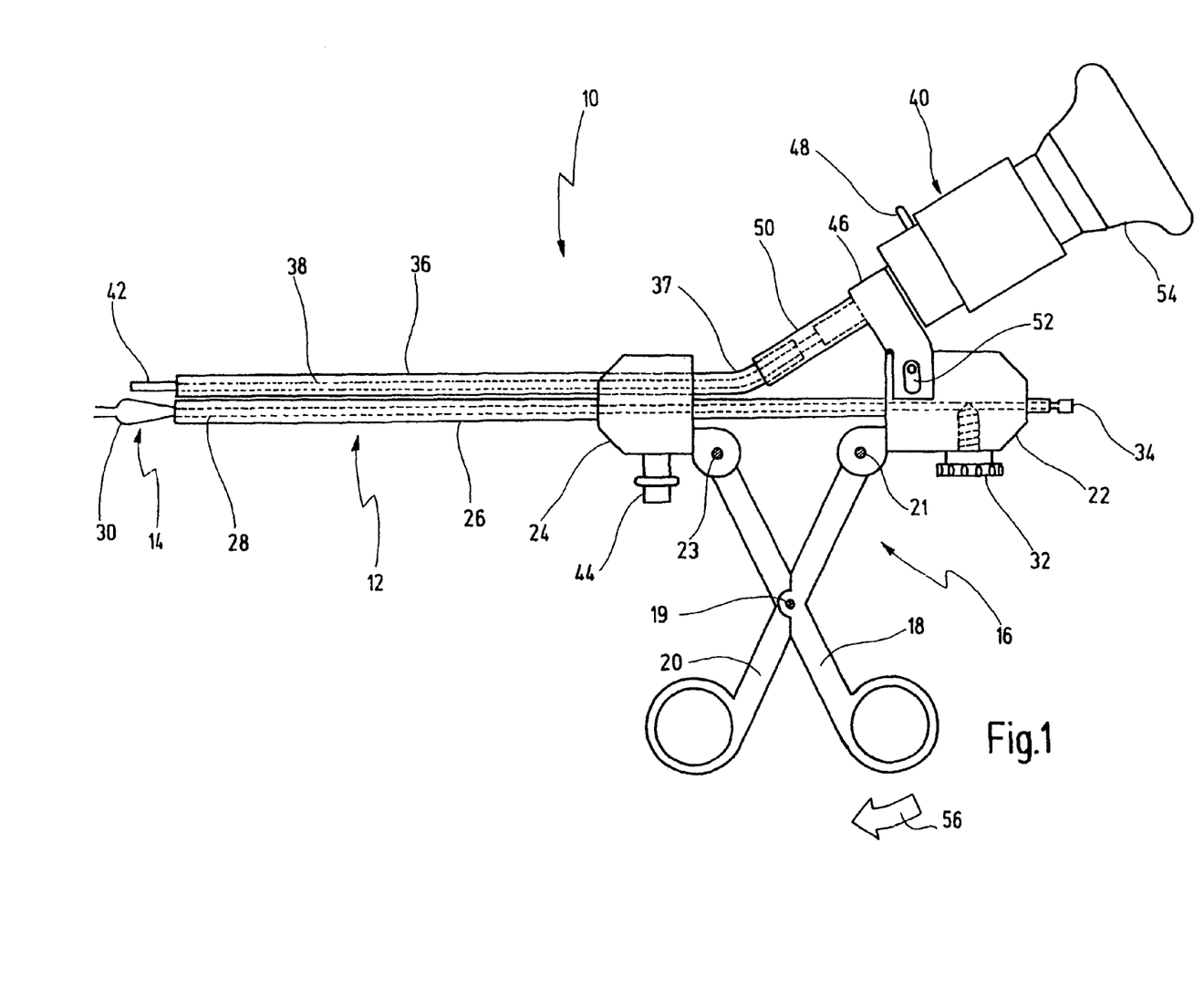
FIG. 1 shows a side view of a medical instrument with an endoscope arranged thereon.

In FIG. 1, a medical instrument is designated in its entirety by reference number 10.

The medical instrument 10 has a shaft 12, at the distal end of which a work element 14 is arranged, and it also has a handle 16. The handle 16 has scissor grip parts 18 and 20 which are connected to one another by a screw 19 so that they can pivot about an axis orthogonal to the scissor grip parts 18, 20. The scissor grip part 18 is connected to a movable part 22 of the instrument 10 via a screw 21 so as to be able to pivot about an axis orthogonal to the scissor grip part 18.

The scissor grip part 20 is connected to an immovable part 24 of the instrument 10 by a screw 23 so as to be able to pivot about an axis orthogonal to the scissor grip part 20.

The immovable part 24 is adjoined at its distal end by a tube 26 which forms the shaft 12. A force transmission element 28, via which the work element 14 is operatively connected to the movable part 22, runs through the tube 26.

The force transmission element 28 serves at the same time as a supply line for feeding HF voltage to the work element 14 which, in this instrument 10, is designed as bipolar forceps 30. At its proximal end, the force transmission element 28 is connected fixedly to the movable part 22 by a clamping element 32. The clamping element 32 is here designed as a screw.

The force transmission element 28 is also in electrical contact with a plug connection 34 located at the proximal end of the movable part 22 in an axial continuation of the shaft 12. An external bipolar HF source can be connected to the force transmission element 28, and thus to the bipolar forceps 30, via the plug connection 34.

The plug connection 34 is here connected fixedly to the force transmission element 28, which is also designed as an electrical conductor. The plug connection 34 is smaller than the clear internal diameter of the shaft 12. Thus, after the screw 32 has been loosened, the work element 14, the force transmission element 28 and the plug connection 34 can be removed as one unit from the instrument 10 by simply pulling it out at the distal end of the shaft 12.

A guide tube 36 is arranged above the shaft 12 and parallel thereto. The guide tube 36 extends through the immovable part 24 and, in the proximal direction from the immovable part 24, has a curved area 37. An endoscope shaft 38 of an endoscope 40 arranged on the instrument 10 extends through the inside of the guide tube 36, a distal end 42 of the endoscope shaft 38 protruding from the guide tube 36 and being located approximately level with the bipolar forceps 30.

The endoscope shaft 38 is flexible. The guide tube 36 not only serves to guide the endoscope shaft 38, it also stabilizes the latter. Because the endoscope shaft 38 is flexible, it is able to adapt to the shape of the curved area 37 of the guide tube 36 when displaced.

The guide tube 36 and the tube 26 communicate with an irrigation attachment piece 44 located on the immovable part 24. Through this irrigation attachment piece 44, irrigation liquid can be passed simultaneously through the tube 26 and the guide tube 36.

At its proximal end, the endoscope 40 is connected to the medical instrument via a securing element 46.

The securing element 46 has a lever 48 with which the securing element 46 can be opened or closed.

At its distal end, the securing element 46 has a telescope tube 50 whose distal end reaches over a proximal end of the guide tube 36. In the area of the movable part 22, the securing element 46 is connected to the movable part 22 via an elongate hole 52. In this way, the securing element 46 is slightly movable transversely with respect to the shaft 12.

The endoscope 40 is secured by inserting the endoscope 40 through the securing element 46, in which process the endoscope shaft 38 is introduced into the guide tube 36, and by activating the lever 48 which shuts off a bayonet closure.

An eyepiece 54 of the endoscope 40 is situated outside the longitudinal axis of the shaft 12, in the continuation of which axis the plug connection 34 is situated.

If the scissor grip part 18 is now moved in the direction of the arrow 56, the movable part 22 is displaced proximally relative to the immovable part 24. In this way, the work element 14 is likewise displaced proximally, i.e. in the direction of the tube 26. The bipolar forceps 30 is thus displaced into the tube 26, as a result of which the jaws of the forceps are moved toward one another, as a result of which the bipolar forceps 30 is closed.

The endoscope 40 is likewise displaced in the proximal direction, as a result of which the distal end 42 of the endoscope shaft 38 is displaced in the direction of the guide tube 36. Because the telescope tube 50 is moved along the curved area 37, the proximal end of the endoscope 40, together with the securing element 46 connected to it, is lifted slightly along the elongate hole 52.

Figure 2:
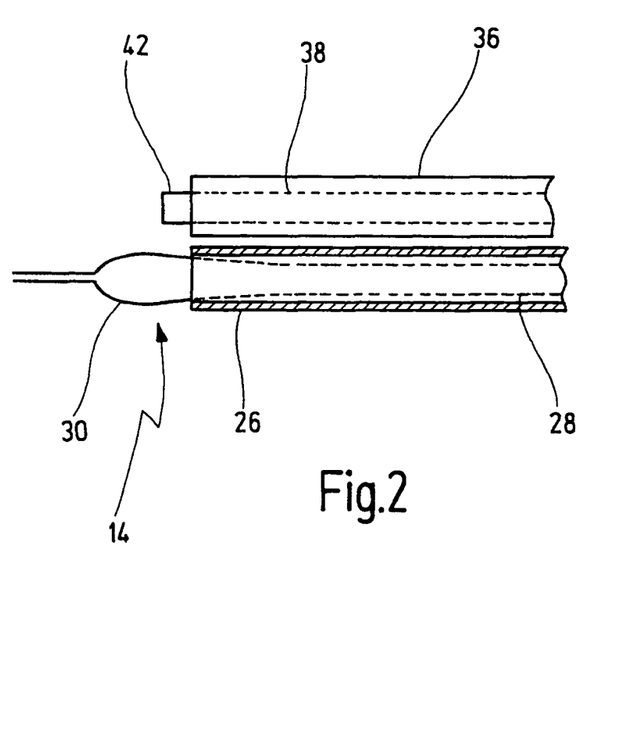
FIG. 2 shows an enlarged view of the distal area of the medical instrument from FIG. 1.

FIG. 2 shows an enlarged view of the distal portion of the medical instrument 10 after the scissor grip part 18 has been moved in the direction of the arrow 56. The work element 14 has been displaced into the tube 26, as a result of which the jaws of the bipolar forceps 30 are pressed together. At the same time, the distal end 42 of the endoscope shaft 38 has been displaced proximally in the direction of the guide tube 36. In this displacement, the distance between the distal end 42 of the endoscope shaft 38 and the bipolar forceps 30 has remained the same.

Figure 3:
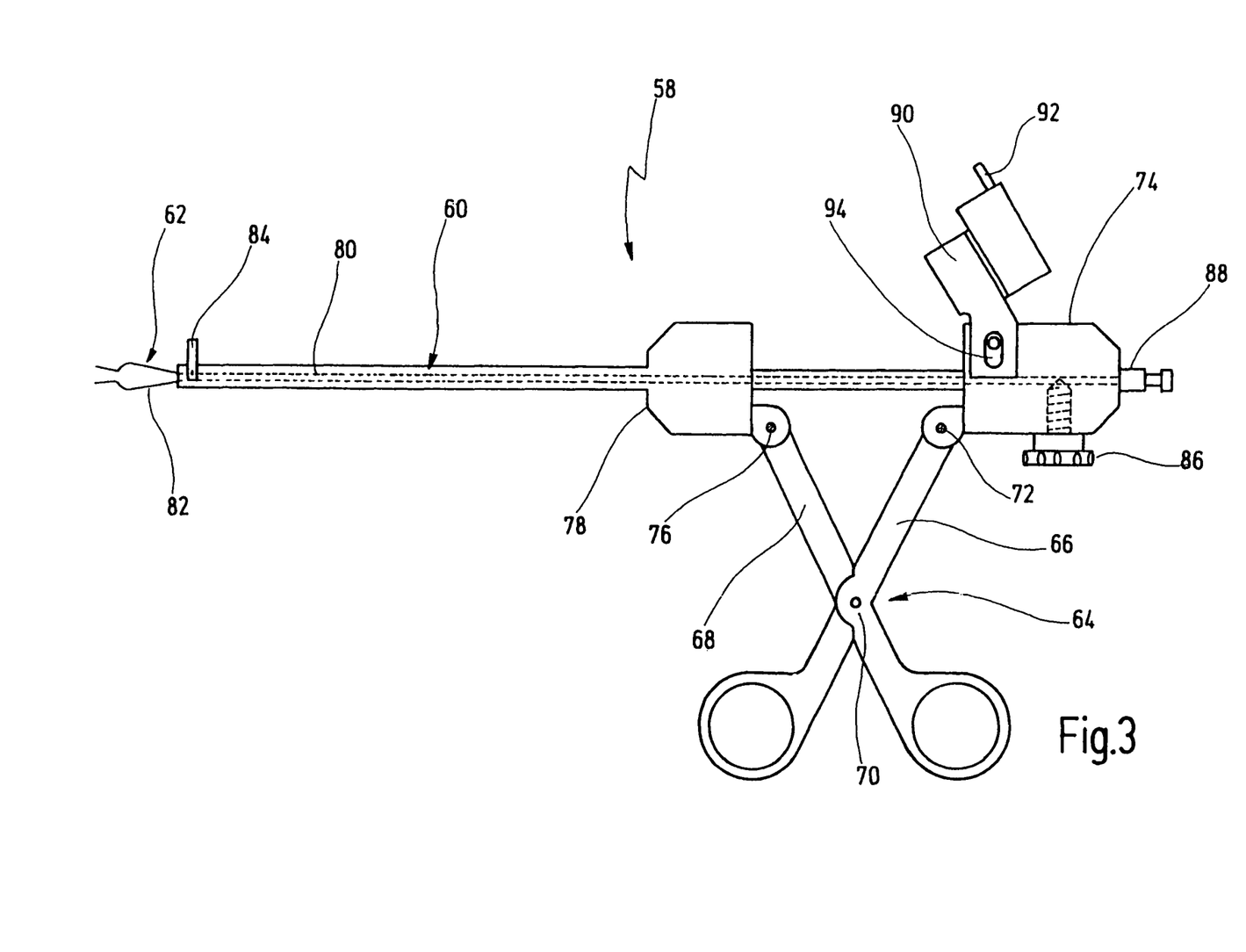
FIG. 3 shows a side view of a further medical instrument.

In FIG. 3, a further illustrative embodiment of a medical instrument is designated in its entirety by reference number 58.

The medical instrument 58 has a shaft 60, at the distal end of which a work element 62 is arranged, and it also has a handle 64. The handle 64 has scissor grip parts 66 and 68 which are connected to one another by a screw 70 so that they can pivot about an axis orthogonal to the plane of the scissor grip parts 66 and 68.

The scissor grip part 66 is connected pivotably to a movable part 74 of the instrument 58 via a screw 72. The scissor grip part 68 is connected to an immovable part 78 of the instrument 58 by a screw 76.

A force transmission element 80 extends through the shaft 60 and is connected at its distal end to the work element 62, which in this case is designed as bipolar forceps 82. The force transmission element 80 serves at the same time as a supply line for feeding HF voltage to the bipolar forceps 82.

Also mounted at the distal end of the shaft 60 there is a securing element 84 for receiving a shaft of an endoscope.

At its proximal end, the force transmission element 80 is connected fixedly to the movable part 74 by a clamping element 86. The clamping element 86 is here designed as a screw. After the screw has been loosened, the bipolar forceps 82, together with the force transmission element 80 connected thereto, can be easily removed from the distal end of the shaft 60 of the medical instrument 58.

The force transmission element 80 is also in electrical contact with a plug connection 88 which is arranged proximally on the movable part 74 in an axial continuation of the shaft 60.

A securing element 90 is also arranged on the movable part 74.

This securing element 90 has a lever 92 with which an endoscope can be connected with force fit to the securing element 90.

In the area of the connection with the movable part 74, the securing element 90 has an elongate hole 94. In this way, the securing element 90 is displaceable, relative to the movable part 74, orthogonally with respect to the shaft 60.

Figure 4:
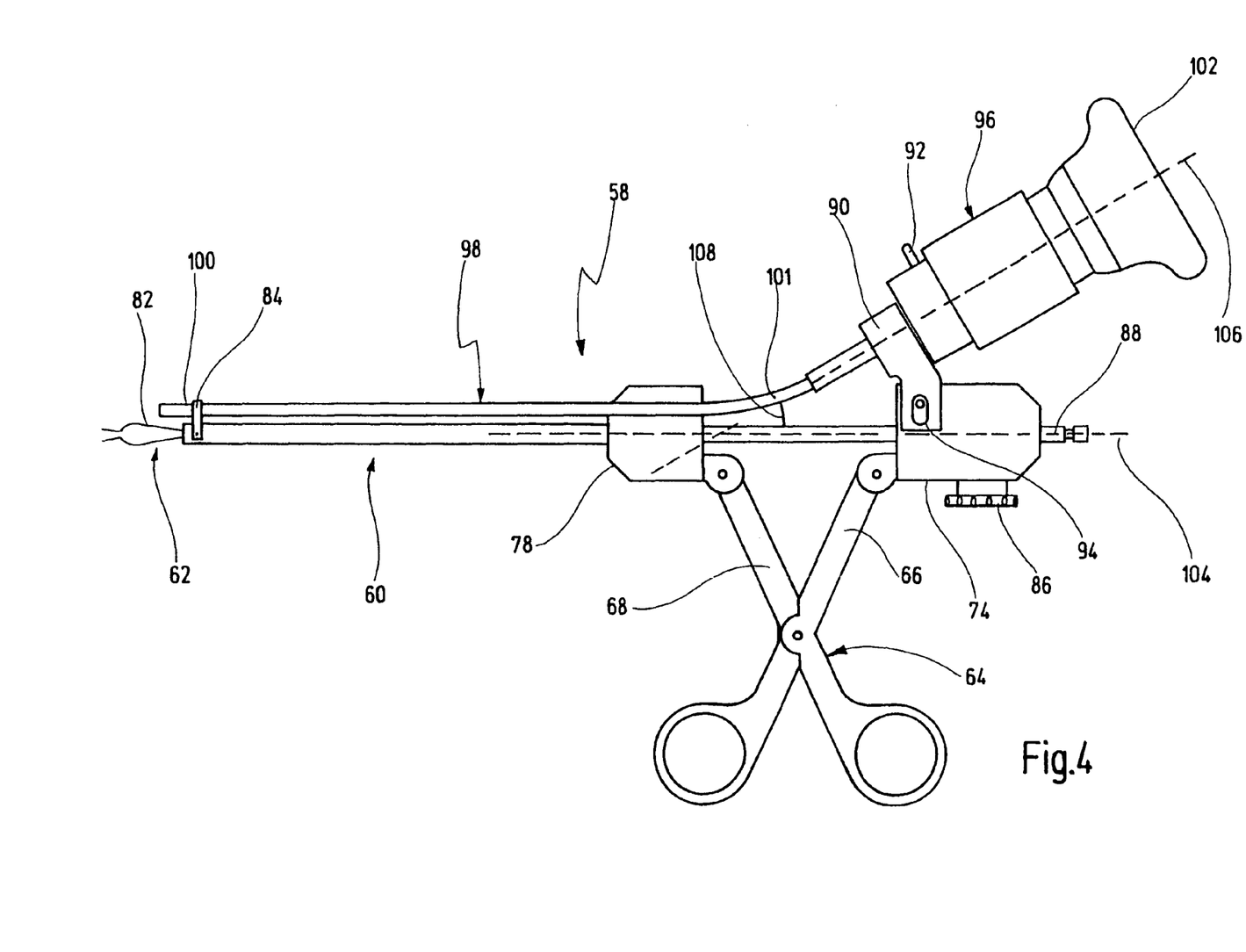
FIG. 4 shows the medical instrument from FIG. 3, with an endoscope arranged thereon.

FIG. 4 shows a medical instrument 58 on which an endoscope 96 has been arranged.

An endoscope shaft 98 of the endoscope 96 here extends substantially parallel to the shaft 60 of the instrument 58. At a distal end 100 of the endoscope shaft 98, the latter is connected to the distal end of the shaft 60 of the medical instrument 58 by the securing element 84.

The distal end 100 of the endoscope shaft 98 protrudes beyond the distal end of the shaft 60 of the instrument 58 and is located approximately level with the bipolar forceps 82. In the proximal area, the endoscope shaft 98 has a curved area 101. By means of this curved area 101, an eyepiece 102 of the endoscope 96 lies outside a longitudinal axis 104 of the shaft 60 of the instrument 58, which axis is here represented by a broken line.

The endoscope shaft 98 is flexible in the area of the curved area 101. A portion of the endoscope shaft 98 distally of the curved area 101 is rigid. Thus, a deflection of the endoscope shaft 98 in the curved area 101 can be changed, in which case the rigid portion can be mounted without additional guide means parallel to the shaft 60 of the endoscope 58.

The longitudinal axis 104 of the shaft 60 forms an angle 108 with a sight line 106 of the eyepiece 102, which sight line is here represented as a broken line.

Since the endoscope shaft 98 is flexible in the curved area 101, the angle 108 can be modified by displacing the securing element 90 along the elongate hole 94, and can be fixed by means not shown here.

What is claimed is:

1. A medical instrument, comprising:
   an endoscope having an endoscopic shaft and an eyepiece,
   an instrument shaft having a distal end, a proximal end and a longitudinal axis,
   a work element arranged at said distal end of said instrument shaft,
   a handle arranged at said proximal end of said instrument shaft and having at least one moveable part for actuating said work element,
   a first securing element for securing said endoscope to said distal end of said instrument shaft in a direction transverse to said longitudinal axis of said instrument shaft, and
   a second securing element for securing said endoscope to said moveable part of said handle such that actuation of said movable part of said handle is configured to displace said endoscope relative to said instrument shaft in a direction of said longitudinal axis of said instrument shaft, said first securing element and said second securing element being designed in such a way that said endoscope is arranged alongside of an outside of said instrument shaft at least between the distal end and the proximal end of the instrument shaft, and
   wherein said eyepiece of said endoscope, in the state when said endoscope is arranged on said instrument shaft, lies outside of said longitudinal axis of said instrument shaft,
   wherein said endoscopic shaft extends from said distal end of said instrument shaft to said second securing element, and
   wherein said endoscopic shaft has a curvature between said first securing element and said second securing element, said eyepiece being at an angle to the longitudinal axis of the instrument shaft.

2. The medical instrument of claim 1, wherein said work element comprises at least one electrode that can be acted upon with HF voltage.

3. The medical instrument of claim 2, wherein said work element is designed as a bipolar work element.

4. The medical instrument of claim 2, wherein said work element communicates with an electrical contact at a proximal end of said handle, said electrical contact lying on said longitudinal axis of said instrument shaft.

5. The medical instrument of claim 4, wherein said work element is connected to said electrical contact via at least one conductor, and said work element, said at least one conductor and said electrical contact can be removed as one unit from said instrument shaft.

6. The medical instrument of claim 4, wherein said electrical contact is designed as a plug connection for attachment of an external cable, said plug connection arranged in a substantially rectilinear continuation of said instrument shaft.

7. The medical instrument of claim 1, wherein said work element is designed as bipolar forceps.

8. The medical instrument of claim 1, further comprising an irrigation attachment piece for simultaneously irrigating an interior of said instrument shaft and an interior of said guide tube.

9. The medical instrument of claim 1, wherein said second securing element is in operative connection with said at least one movable part of said handle.

10. The medical instrument of claim 1, wherein upon actuation of said handle, said second securing element holds said distal end of said endoscopic shaft at a constant distance from said work element.

11. The medical instrument of claim 1, wherein said handle comprises at least one grip protruding laterally from said instrument shaft.

12. The medical instrument of claim 11, wherein said grip of said handle is designed in the manner of scissor grip parts.

13. The medical instrument of claim 1, wherein said endoscopic shaft is bendable at least in an area of said curvature.

14. A medical instrument, comprising: an endoscope having an endoscopic shaft and an eyepiece, an instrument shaft having a distal end, a proximal end and a longitudinal axis, a work element arranged at said distal end of said instrument shaft, a handle arranged at said proximal end of said instrument shaft and having at least one moveable part for actuating said work element, a force transmission element movable relative to said instrument shaft in a direction of said longitudinal axis of said instrument shaft and extending through said instrument shaft and connecting said work element with said at least one movable part of said handle, a first securing element for securing said endoscope to said distal end of said instrument shaft in a direction transverse to said longitudinal axis of said instrument shaft, and a second securing element for securing said endoscope to said moveable part of said handle such that actuation of said movable part of said handle is configured to displace said endoscope together with said force transmission element relative to said instrument shaft in a direction of said longitudinal axis of said instrument shaft, said first securing element and said second securing element being designed in such a way that said endoscope is arranged alongside of an outside of said instrument shaft at least between the distal end and the proximal end of the instrument shaft, wherein said eyepiece of said endoscope, in the state when said endoscope is arranged on said instrument shaft, lies outside of said longitudinal axis of said instrument shaft, wherein said first securing element has a guide tube for said endoscopic shaft, said guide tube arranged on said instrument shaft, said endoscopic shaft being insertable into said guide tube, wherein said guide tube extends from said distal end of said instrument shaft to said second securing element, and wherein said guide tube has a curved area distally of said second securing element, said eyepiece being at an angle to the longitudinal axis of the instrument shaft.

15. A medical instrument, comprising:
an endoscope having an endoscopic shaft and an eyepiece,
an instrument shaft having a distal end, a proximal end and a longitudinal axis,
a work element arranged at said distal end of said instrument shaft,
a handle arranged at said proximal end of said instrument shaft and having at least one moveable part for actuating said work element,
a first securing element for securing said endoscope to said distal end of said instrument shaft in a direction transverse to said longitudinal axis of said instrument shaft, said first securing element having a guide tube for said endoscopic shaft, said guide tube arranged on said instrument shaft, said endoscopic shaft being insertable into said guide tube, and
a second securing element for securing said endoscope to said moveable part of said handle such that actuation of said movable part of said handle is configured to displace said endoscope relative to said instrument shaft in a direction of said longitudinal axis of said instrument shaft, said first securing element and said second securing element being designed in such a way that said endoscope is arranged alongside of an outside of said instrument shaft at least between the distal end and the proximal end of the instrument shaft, and
wherein said eyepiece of said endoscope, in the state when said endoscope is arranged on said instrument shaft, lies outside of said longitudinal axis of said instrument shaft,
wherein said guide tube extends from said distal end of said instrument shaft to said second securing element, and
wherein said guide tube has a curved area distally of said second securing element, said eyepiece being at an angle to the longitudinal axis of the instrument shaft.

* * * * *